United States Patent [19]

Neeb et al.

[11] Patent Number: 4,618,701

[45] Date of Patent: Oct. 21, 1986

[54] PROCESS FOR PREPARING 6-ACETOXY-2-NAPHTHOIC-ACID AND PURE 6-HYDROXY-2-NAPHTHOIC ACID

[75] Inventors: Rudolf Neeb, Offenbach am Main; Wolfgang Ironich, Eppstein/Taunus; Heinrich Volk, Bad Vilbel, all of Fed. Rep. of Germany

[73] Assignee: Hoechst Aktiengesellschaft, Fed. Rep. of Germany

[21] Appl. No.: 705,626

[22] Filed: Feb. 26, 1985

[30] Foreign Application Priority Data

Feb. 28, 1984 [DE] Fed. Rep. of Germany ....... 3407100

[51] Int. Cl.$^4$ .................... C07C 67/08; C07C 69/145
[52] U.S. Cl. .................... 560/139; 562/467
[58] Field of Search .................... 560/139; 562/467

[56] References Cited

U.S. PATENT DOCUMENTS 4,161,470  7/1979  Calundann .................... 528/173
4,219,461  8/1980  Calundann .................... 560/139

FOREIGN PATENT DOCUMENTS 2911667  10/1980  Fed. Rep. of Germany ...... 562/467

OTHER PUBLICATIONS

Butler et al., *J. Chem. Soc.* 123:1649–1655 (1923), particularly p. 1653.
Lesser et al., *Ber.* 58:2109–2117 (1925), particularly p. 2116.
Gradenwitz, *Ber.* 27:2621–2624 (1894), particularly p. 2624.
Miller, *Ber.* 14:1600–1602 (1881), particularly p. 1602, note 1.

*Primary Examiner*—Werren B. Lone
*Attorney, Agent, or Firm*—Connolly and Hutz

[57] ABSTRACT

6-Hydroxy-2-naphthoic acid can be selectively acetylated to 6-acetoxy-2-naphthoic acid, in particular in the presence of admixtures of isomeric hydroxy-naphthoic acids, and thus be separated from those isomeric admixtures. The acetylation is affected in aqueous alkaline solution by reaction with acetic anhydride. By hydrolysis of the 6-acetoxy-2-naphthoic acid, a pure 6-hydroxy-2-naphthoic acid is obtained.

24 Claims, No Drawings

PROCESS FOR PREPARING 6-ACETOXY-2-NAPHTHOIC-ACID AND PURE 6-HYDROXY-2-NAPHTHOIC ACID

The invention is in the technical field of the preparation of intermediates which can be processed, for example, to plastics. It relates to a process for preparing 6-acetoxy-2-naphthoic acid, more particularly to a process for separating 6-hydroxy-2-naphthoic acid from isomeric hydroxynaphthoic acids by (selectively) converting 6-hydroxy-2-naphthoic acid into the corresponding 6-acetoxy-2-naphthoic acid with optionally subsequent hydrolysis.

6-Acetoxy-2-naphthoic acid has for some years attained increasing importance for the production of synthetic fibers and plastics having useful technical properties (cf. for example U.S. Pat. No. 4,161,470, in particular column 7, lines 23–39 and 51–67, and Example I, and U.S. Pat. No. 4,219,461). Yet, the literature contains only very general statements on the synthesis of 6-acetoxy-2-naphthoic acid. For instance, J. Chem. Soc. (London) 123, 1653 (1923), merely reveals that 6-acetoxy-2-naphthoic acid is prepared from 6-hydroxy-2-naphthoic acid "by means of acetic anhydride". This measure must evidently be understood as meaning that 6-hydroxy-2-naphthoic acid is heated with acetic anhydride at the boil for a prolonged period, since this acetylation method was already practised in preparing 2-acetoxynaphthalene from 2-naphthol (see Berichte der dt. Chem. Ges. 14 (1881), 1602, Note 1) and in preparing 3-acetoxy-2-naphthoic acid from 3-hydroxy-2-naphthoic acid (see Ber. loc. cit. 27, 2624 (1894); later also in Ber. 58, 2116 (1925)).

The state of the art thus teaches that 6-acetoxy-2-naphthoic acid can be synthesized by acetylating 6-hydroxy-2-naphthoic acid by means of acetic anhydride in the absence of water within the acid range at temperatures of above 100° C., generally at the boiling point of the acetylation mixture.

In contrast to the preparation of 6-acetoxy-2-naphthoic acid, however, the preparation of its starting material, namely 6-hydroxy-2-naphthoic acid, effected by Kolbe-Schmitt reaction from potassium β-naphtholate and carbon dioxide, has been described in great detail (see U.S. Pat. Nos. 1,593,816 and 4,287,357). However, the preparation of 6-hydroxy-2-naphthoic acid by the Kolbe-Schmitt reaction is unavoidably accompanied by the formation of more or less sizeable amounts of isomeric hydroxynaphthalene monocarboxylic acids and hydroxynaphthalene dicarboxylic acids, in particular for example the formation of 3-hydroxy-2-naphthoic acid. It is true that these proportions of undesirable isomeric hydroxynaphthoic acids can be suppressed to a certain degree by conducting the reaction in a suitable manner, but the desired 6-hydroxy-2-naphthoic acid is only obtainable in pure form by this method by initially following the example of U.S. Pat. No. 1,593,816 or Example 1 of U.S. Pat. No. 4,287,357 and utilizing the different solubility properties of the isomeric compounds and separating out the 6-hydroxy-2-naphthoic acid either from hot water or in dilute mineral acid at a certain pH.

According to the abovementioned state of the art, the synthesis of 6-acetoxy-2-naphthoic acid may involve three separate stages or steps, namely, first, an expensive purifying separation of the 6-hydroxy-2-naphthoic acid formed by Kolbe-Schmitt reaction from its hydroxynaphthoic acid isomer, drying the isolated product, and then converting it into the desired 6-acetoxy-2-naphthoic acid by heating in the presence of excess acetic anhydride. The final yield taken over all these steps is naturally not satisfactory.

There is therefore a need for a process which permits in a simple way the preparation of isomerically pure 6-acetoxy-2-naphthoic acid in optimal yield.

It has now been found that 6-hydroxy-2-naphthoic acid can be converted into a 6-acetoxy-2-naphthoic acid in a simple manner and, what is more, selectively from isomeric admixtures by reacting an aqueous alkaline solution of an alkali metal salt, preferably dialkali metal salt, of 6-hydroxy-2-naphthoic acid, which may also contain admixtures of isomeric hydroxynaphthoic acids, for instance the aqueous alkaline solutions of a carboxylation product of potassium β-naphtholate, with acetic anhydride.

The procedure according to the invention, namely acetylating 6-hydroxy-2-naphthoic acid in aqueous alkaline solution with acetic anhydride, and thus also being able to dispense with reaction temperatures of above 100° C., has especially the great advantage that the isomeric hydroxynaphthoic acids present in the aqueous solution at the same time, in particular 3-hydroxy-2-naphthoic acid, surprisingly do not react with acetic anhydride, so that the 6-hydroxy-2-naphthoic acid is readily acetylated selectively and can be separated from the other hydroxynaphthoic acids. The present invention thus also relates to the separation of 6-hydroxy-2-naphthoic acid from its isomeric compounds by selective acetylation; after its isolation the 6-acetoxy compound can be hydrolyzed if desired or if necessary to the 6-hydroxy compound by conventional methods, thus obtaining a pure 6-hydroxy-2-naphthoic acid.

The alkali metal salts of 6-hydroxy-2-naphthoic acid which are used as the starting compounds in aqueous solution are preferably the sodium and potassium salts.

The acetylation reaction is carried out within the strongly alkaline range, preferably at pH 10 or higher, such as at pH 10–13, in particular at pH 11.5–12.5. The reaction temperature of the acetylation can be below 60° C., and is preferably below 50° C., since at distinctly higher temperatures the hydrolysis of acetic anhydride to acetic acid comes undesirably to the fore. In relation thereto, to avoid too high an excess of acetic anhydride, the acetylation should therefore be carried out at a temperature between 10° and 40° C., preferably between 15° and 30° C., in particular between 20° and 25° C., thus within the range of room temperature.

The acetylation reaction according to the invention can in principle be carried out in satisfactory yields using equimolar amounts of acetic anhydride and 6-hydroxy-2-naphthoic acid. However, acetic anhydride is preferably used in excess, for instance in up to 3.5-fold molar excess, since the use of excess acetic anhydride is advantageous for the subsequent working-up operations. The acetic anhydride level is thus as a rule chosen to be such that the amount of acetic acid liberated by the acetylation on the one hand and by the hydrolysis of the excess acetic anhydride on the other is sufficient to bring the reaction mixture to a pH between about 6.0 and 4.0, in particular between 5.5 and 4.5, without a need for extra acid to be added subsequently, in a further operation. The pH after the acetylation reaction can of course also be brought about with a different acid, such as an organic or inorganic acid customary for this purpose.

The acetic anhydride is generally used in an amount of 1.2 to 3.0 moles, preferably 1.5 to 2.5 moles, per mole of 6-hydroxy-2-naphthoic acid.

The 6-acetoxy-2-naphthoic acid obtainable by the process according to the invention is precipitated from the reaction mixture at the abovementioned pH of between about 6.0 and 4.0 and is isolated, for example by filtration. If the resulting filtrate is brought to a pH between 2 and 1 by addition of acid, for example dilute sulfuric acid, the naphthoic acids not acetylated under the reaction conditions according to the invention and still in solution, such as in particular 3-hydroxy-2-naphthoic acid, can likewise be precipitated and isolated.

A simple way of preparing the aqueous starting solution of the alkali (dialkali) metal salts of 6-hydroxy-2-naphthoic acid comprises, for example, dissolving 6-hydroxy-2-naphthoic acid either in pure form or mixed with isomeric admixtures, such as, for example, 3-hydroxy-2-naphthoic acid (mixtures like this are obtained for example in working up the aqueous mother liquor by the method of Example 1 of U.S. Pat. No. 4,287,357), in aqueous alkali metal hydroxide which preferably contains 2 moles of alkali metal hydroxide per mole of hydroxynaphthoic acid. The concentration of the alkali (dialkali) metal salts in this aqueous alkaline solution generally depends on their solubility at whichever temperature is used; thus, 6-hydroxy-2-naphthoic acid can generally be used in the acetylation batch between about 20° and 40° C. in up to 20% by weight strength aqueous solution, preferably in 3 to 10% by weight strength solution.

A particularly preferred form of the process according to the invention is thus the selective acetylation of 6-hydroxy-2-naphthoic acid in aqueous alkaline solutions of hydroxynaphthoic acids, such as aqueous alkaline solutions of carboxylation batches of potassium β-naphtholate or of mixtures of potassium and sodium β-naphtholate, which have been worked up by literature-described methods following prior removal of resinous matter and unconverted β-naphthol and contain hydroxynaphthoic acid isomers as byproducts, in particular 3-hydroxy-2-naphthoic acid as a byproduct.

If the acetylation according to the invention is carried out in the presence of other hydroxy-2-naphthoic acid isomers, acetic anhydride is generally used in the reaction in an amount which, corresponding to the abovementioned figures, is calculated relative to the total amount of hydroxy-2-naphthoic acid isomers, and thus is generally between equimolar and 3.5-times the molar amount, preferably 1.2- to 3.0-times and particularly preferably between 1.5- and 2.5-times the molar amount, based on the total amount of hydroxy-2-naphthoic acid isomers.

The 6-acetoxy-2-naphthoic acid can, as already mentioned above, then be hydrolyzed to form the 6-hydroxy-2-naphthoic acid. By this way, the 6-hydroxy-2-naphthoic acid is obtained as a very pure product. It is thus possible to purify impure 6-hydroxy-2-naphthoic acid or a 6-hydroxy-2-naphthoic acid product containing isomeric compounds thereof, by means of the acetylation reaction and subsequent hydrolysis in good yields in a relatively simple manner. This procedure has significant advantages in comparison to the purification procedure by recrystallization which has been carried out according to the U.S. Pat. No. 1,553,816. The present invention thus also concerns a process for the preparation of pure 6-hydroxy-2-naphthoic acid or, respectively, a process for the purification of impure 6-hydroxy-2-naphthoic acid, in particularly soiled with isomeric hydroxy naphthoic acid compounds, which is characterized by that the impure 6-hydroxy-2-naphthoic acid is firstly acetylated according to the above recited procedure according to the invention, and the isolated 6-acetoxy-2-naphthoic acid is then hydrolyzed.

The hydrolysis reaction of 6-acetoxy-2-naphthoic acid to form 6-hydroxy-2-naphthoic acid can be followed in a manner which is known as such, such as in aqueous alkaline or in aqueous acidic medium. A solvent which is inert to the reaction conditions in this reaction batch and which is soluble in water or can be mixed with water, can be added to the reaction medium, in particular if the hydrolysis is carried out in aqueous acidic medium, in order to improve the solubility of the 6-acetoxy-2-naphthoic acid in the reaction medium. Those solvents are in particular straight-chained or branched alkanols of from 1 to 5 carbon atoms, such as ethanol.

The aqueous alkaline medium for the hydrolysis reaction can be, for example, an aqueous ammonium hydroxide solution or an aqueous alkali metal hydroxide solution, such as an aqueous sodium hydroxide solution. In general, the alkaline agent is used in such an amount which is sufficient to dissolve the 6-acetoxy-2-naphthoic acid. The alkaline hydrolysis reaction is carried out preferably at a temperature between 50° and 105° C., in particular between 75° and 95° C., and at a pH between 8 and 14, in particular between 11 and 13. When the alkaline hydrolysis is ended, the formed 6-hydroxy-2-naphthoic acid is precipitated—optionally after a clarification of the solution by means of common clarification agents, such as charcoal, and subsequent filtration—by means of an acid, for example an aqueous mineral acid, such as hydrochloric acid or preferably sulfuric acid. Precipitation can be made at a pH between 4 and 1. The precipitated 6-hydroxy-2-naphthoic acid can then be isolated in the usual manner.

The hydrolysis reaction of the 6-acetoxy-2-naphthoic acid can be carried out in the aqueous acidic medium, in general with the use of an aqueous mineral acid, such as aqueous hydrochloric acid and in particular aqueous sulfuric acid. In this acidic medium, the concentration of the aqueous acid can be varied in wide ranges; usually, a 1% to 50% by weight aqueous mineral acid, such as aqueous sulfuric acid, is used as reaction medium; preferably, a 10% to 30% by weight, in particular a 15% to 20% by weight aqueous acid is used. The pH of the reaction medium is, in general, less than 1.5, for example at about 1 and less than 1. The hydrolysis reaction is, in general, carried out at a temperature between 50° and 110° C., in particular between 85° and 105° C. The 6-hydroxy-2-naphthoic acid which has been formed precipitates from the acid hydrolysis medium and can be isolated in the usual manner.

The following examples serve to illustrate the invention in more detail. The parts and percentages are by weight, unless otherwise stated. The purity was determined by high pressure liquid chromatography (HPLC).

EXAMPLE 1

20.4 parts (0.2 mole) of acetic anhydride are stirred at a temperature between 20° and 25° C. into a solution of 37.6 parts (0.2 mole) of 6-hydroxy-2-naphthoic acid in 750 parts of 2.2% strength aqueous sodium hydroxide solution (this starting solution has a pH of about 12.5). The reaction batch is afterwards stirred for a further hour and is then brought to a pH of 4.5–5 with dilute aqueous sulfuric acid. The precipitated product is filtered off with suction, is washed with water and is dried.

Yield of 6-acetoxy-2-naphthoic acid: 45.2 parts of about 99% purity, which corresponds to 98% of theory.

EXAMPLE 2

61.2 parts (0.6 mole) of acetic anhydride are stirred at a temperature between 20° and 25° C. into a solution of 37.6 parts of 6-hydroxy-2-naphthoic acid in 750 parts of 2.2% strength aqueous sodium hydroxide solution. The reaction batch is afterwards stirred for a further hour and the product which has precipitated at pH 4.5–5.5 is filtered off with suction, is washed with water and is dried.

Yield of 6-acetoxy-2-naphthoic acid: 44.4 parts of about 99.5% purity, which corresponds to 96.5% of theory.

Examples 3 to 5 demonstrate the selective acetylation of 6-hydroxy-2-naphthoic acid in mixtures of 6-hydroxy-2-naphthoic acid and 3-hydroxy-2-naphthoic acid of different compositions:

EXAMPLE 3

92 parts (0.9 mole) of acetic anhydride are stirred at a temperature between 20° and 25° C. into a solution of a mixture of 90 parts (0.478 mole) of 6-hydroxy-2-naphthoic acid and 10 parts of 3-hydroxy-2-naphthoic acid in 2000 parts of 2.2% strength aqueous sodium hydroxide solution (this starting solution has a pH of about 12.5). The reaction batch is afterwards stirred for a further hour and the product which has precipitated at pH 4.5–5.5 is filtered off with suction, is washed with water and is dried.

Yield of 6-acetoxy-2-naphthoic acid: 104.5 parts of about 99% purity, which corresponds to 98% of theory.

The filtrate can be worked up for the byproducts. For this, it is brought to pH 2 with dilute aqueous sulfuric acid, and the precipitated product is isolated (for example by filtration) and dried. The result is 8.5 parts of a product of 91% pure 3-hydroxy-2-naphthoic acid; the "impurities" are in the main unreacted 6-hydroxy-2-naphthoic acid.

EXAMPLE 4

50 parts of acetic anhydride are stirred at a temperature between 20° and 25° C. into a solution of a mixture of 50 parts of 6-hydroxy-2-naphthoic acid and 50 parts of 3-hydroxy-2-naphthoic acid in a mixture of 2000 parts of water and 93 parts of a 45% strength aqueous sodium hydroxide solution (this solution has a pH of about 12.5). The reaction batch is afterwards stirred for a further hour and the product which has precipitated at pH of 5.5–6.0 is filtered off with suction, is washed with water and is dried.

Yield of 6-acetoxy-2-naphthoic acid: 57.5 parts of about 99% purity, which corresponds to 94% of theory.

The filtrate is worked up as in Example 3 to yield about 50 parts of a product which contains about 95% of 3-hydroxy-2-naphthoic acid; the "impurities" are in the main unreacted 6-hydroxy-2-naphthoic acid.

EXAMPLE 5

45 parts of acetic anhydride are stirred at a temperature between 20° and 25° C. into a solution at about pH 12.5 of a mixture of 10 parts of 6-hydroxy-2-naphthoic acid and 90 parts of 3-hydroxy-2-naphthoic acid in 2000 parts of a 2% strength aqueous sodium hydroxide solution. The reaction batch is afterwards stirred for a further hour and the product which has precipitated at pH of about 5.0–5.5 is filtered off with suction, is washed with water and is dried.

Yield of 6-acetoxy-2-naphthoic acid: 9.1 parts of about 98% purity.

The filtrate is worked up as in Example 3 to yield about 94 parts of a product which contains about 95% of 3-hydroxy-2-naphthoic acid; the "impurities" are in the main unreacted 6-hydroxy-2-naphthoic acid.

EXAMPLE 6

728 parts of anhydrous potassium salt of 2-hydroxynaphthalene are carboxylated using a known carboxylation method, for example at a temperature between 250° and 270° C. and under a carbon dioxide pressure of 3 to 4 bar. The carboxylation melt is dissolved with about 7000 parts of water, and the solution is brought to pH 6.5 at 80° C. with mineral acid, such as hydrochloric acid. The resin formed and small amounts of 2-hydroxynaphthalene are separated off as described for example in German Offenlegungsschrift No. 2,911,667.

The aqueous solution is then brought to a pH of 12.5 with aqueous sodium hydroxide solution; 270 parts of acetic anhydride are added at a temperature of between 20° and 25° C. with stirring, and the mixture is afterwards stirred for about a further hour during which the pH gradually drops to 6.5–6.0.

The precipitated product is isolated, is washed with water and is dried under reduced pressure, affording 330 parts of 6-acetoxy-2-naphthoic acid having a purity of above 99%.

The filtrate can be worked up for byproducts. For this it is brought to pH 2 with dilute aqueous sulfuric acid, and the precipitated product is isolated and dried, affording 60 parts of a product mixture which chiefly consists of 3-hydroxy-2-naphthoic acid.

EXAMPLE 7

100 parts of a moist 6-acetoxy-2-naphthoic acid containing 60 parts of water, such as obtainable, for example, according to the above Example 6 before this product has been dried, are stirred in 300 parts of an about 70% aqueous sulfuric acid solution at a temperature between 90° and 100° C. for 4 hours. The 6-hydroxy-2-naphthoic acid which is formed and which precipitates, is filtered off after the reaction batch has been cooled to 70° to 80° C., washed with hot water and dried. 31 parts of a pure 6-hydroxy-2-naphthoic acid is obtained, having a melting point of 245° C. (according to Example 1 of U.S. Pat. No. 1,593,816, recrystallized 6-hydroxy-2-naphthoic acid has a melting point of 245° C.).

EXAMPLE 8

In order to hydrolyze 6-acetoxy-2-naphthoic acid, the procedure according to Example 7 is followed, however, 500 parts of an about 10% aqueous sulfuric acid with the addition of 20 parts of ethanol is used in place of the 70% sulfuric acid. 28.9 parts of pure 6-hydroxy-2-naphthoic acid, having a melting point of 245° C. is obtained.

EXAMPLE 9

100 parts of a moist 6-acetoxy-2-naphthoic acid, such as obtainable according to the above Example 6 before drying, with a content of 60 parts of water is heated in 500 parts of an about 3.5% aqueous sodium hydroxide solution for 2 hours with stirring. Thereafter, the solution obtained is clarified by treatment with 5 parts of charcoal and subsequent filtration. About 40 parts of an about 50% aqueous sulfuric acid is added to the filtrate, and the precipitated 6-hydroxy-2-naphthoic acid is isolated at a temperature between 70° and 80° C., for example by filtration. The isolated product is washed with hot water; after drying, 30 parts of pure 6-hydroxy-2-naphthoic acid having a melting point of 245° C., is obtained.

We claim:

1. A process for preparing 6-acetoxy-2-naphthoic acid which comprises reacting an alkali metal salt of 6-hydroxy-2-naphthoic acid in aqueous alkaline solution with acetic anhydride at a pH of at least 10 and at a temperature below 50° C., with the use of 1 to 3.5 moles of acetic anhydride per mole of 6-hydroxy-2-naphthoic acid.

2. The process according to claim 1, wherein the aqueous alkaline solution of 6-hydroxy-2-naphthoic acid contains admixtures of one or more hydroxynaphthoic acid isomers in dissolved form.

3. The process according to claim 2 wherein the or one of the hydroxynaphthoic acid isomers is 3-hydroxy-2-naphthoic acid.

4. A process for separating 6-hydroxy-2-naphthoic acid from its isomeric hydroxynaphthoic acids by acetylation of 6-hydroxy-2-naphthoic acid, in its alkali metal salt form, with 1 to 3.5 moles of acetic anhydride per mole of 6-hydroxy-2-naphthoic acid, at a pH of at least 10 and a temperature below 50° C.

5. The process according to claim 4 wherein the or one of the hydroxynaphthoic acid isomers is 3-hydroxy-2-naphthoic acid.

6. The process according to claim 4, wherein the acetylation is carried out at a pH of 10 to 13.

7. The process according to claim 1, wherein the acetylation is carried out at a pH between 11.5 and 12.5.

8. The process according to claim 4, wherein the acetylation is carried out at a pH between 11.5 and 12.5.

9. The process according to claim 1, wherein the reaction is carried out at a temperature between 15° and 30° C.

10. The process according to claim 4, wherein the reaction is carried out at a temperature between 15° and 30° C.

11. The process according to claim 1, wherein the acetylation is carried out using 1.2 to 3.0 moles of acetic anhydride per mole of 6-hydroxy-2-naphthoic acid.

12. The process according to claim 4, wherein the acetylation is carried out using 1.2 to 3.0 moles of acetic anhydride per mole of 6-hydroxy-2-naphthoic acid.

13. The process according to claim 4 for separating 6-hydroxy-2-naphthoic acid in the form of 6-acetoxy-2-naphthoic acid from isomeric hydroxynaphthoic acids, in particular from 3-hydroxynaphthoic acid, wherein an aqueous alkaline solution of alkali metal salts of 6-hydroxy-2-naphthoic acid which contains the isomeric hydroxynaphthoic acids is reacted with acetic anhydride, and the resulting 6-acetoxy-2-naphthoic acid is then precipitated at a pH between about 6.0 and 4.0 and is isolated.

14. The process according to claim 1, wherein the aqueous alkaline solutions of hydroxynaphthoic acids, including 6-hydroxy-2-naphthoic acid, are the aqueous alkaline solutions obtainable from a carboxylation of potassium β-naphtholate.

15. The process according to claim 4, wherein the aqueous alkaline solutions of hydroxynaphthoic acids, including 6-hydroxy-2-naphthoic acid, are the aqueous alkaline solutions obtainable from a carboxylation of potassium β-naphtholate.

16. A process according to claim 1 for the preparation of pure 6-hydroxy-2-naphthoic acid from impure 6-hydroxy-2-naphthoic acid, which comprises firstly acetylating the soiled 6-hydroxy-2-naphthoic acid according to a procedure of claim 1, isolating the 6-acetoxy-2-naphthoic acid formed, and hydrolyzing it in an aqueous medium.

17. A process according to claim 4 for the preparation of pure 6-hydroxy-2-naphthoic acid from impure 6-hydroxy-2-naphthoic acid, which comprises firstly acetylating the soiled 6-hydroxy-2-naphthoic acid according to a procedure of claim 4, isolating the 6-acetoxy-2-naphthoic acid formed, and hydrolyzing it in an aqueous medium.

18. A process according to claim 16, wherein the hydrolysis reaction is carried out in an aqueous mineral acid.

19. A process according to claim 17, wherein the hydrolysis reaction is carried out in an aqueous mineral acid.

20. A process according to claim 16, wherein the hydrolysis reaction is carried out in an aqueous alkali metal hydroxide solution.

21. A process according to claim 17, wherein the hydrolysis reaction is carried out in an aqueous alkali metal hydroxide solution.

22. A process according to claim 16, wherein the hydrolysis reaction is carried out in the presence of a straight-chained or branched alkanol of from 1 to 5 carbon atoms.

23. A process according to claim 17, wherein the hydrolysis reaction is carried out in the presence of a straight-chained or branched alkanol of from 1 to 5 carbon atoms.

24. The process according to claim 13, wherein, after isolating the 6-acetoxy-2-naphthoic acid, the filtrate is brought to a pH between 1 to 2 and the precipitated isomeric hydroxy-naphthoic acids, including 3-hydroxy-2-naphtholic acid, are isolated.

* * * * *